United States Patent
Schulte et al.

(10) Patent No.: US 9,110,009 B2
(45) Date of Patent: Aug. 18, 2015

(54) GRADIENT INDEX (GRIN)-BASED ABSORPTION SPECTROSCOPY APPARATUS, METHOD, AND APPLICATIONS

(75) Inventors: Alfons Schulte, Orlando, FL (US); Silki Arora, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 507 days.

(21) Appl. No.: 13/425,670

(22) Filed: Mar. 21, 2012

(65) Prior Publication Data

US 2012/0242992 A1 Sep. 27, 2012

Related U.S. Application Data

(60) Provisional application No. 61/454,785, filed on Mar. 21, 2011.

(51) Int. Cl.
*G01N 21/31* (2006.01)

(52) U.S. Cl.
CPC ............ *G01N 21/31* (2013.01); *G01N 2201/08* (2013.01); *G01N 2201/0866* (2013.01)

(58) Field of Classification Search
USPC ................................. 356/432–444
See application file for complete search history.

(56) References Cited

U.S. PATENT DOCUMENTS

| | | | | |
|---|---|---|---|---|
| 3,744,918 A * | 7/1973 | Jacobsson | | 356/418 |
| 4,534,616 A * | 8/1985 | Bowen et al. | | 385/79 |
| 5,048,959 A * | 9/1991 | Morris et al. | | 356/301 |
| 5,155,549 A * | 10/1992 | Dhadwal | | 356/336 |
| 5,456,252 A * | 10/1995 | Vari et al. | | 600/301 |
| 5,713,364 A * | 2/1998 | DeBaryshe et al. | | 600/476 |
| 5,719,973 A * | 2/1998 | Monroe et al. | | 385/34 |
| 5,736,410 A * | 4/1998 | Zarling et al. | | 436/172 |
| 6,075,592 A * | 6/2000 | Banerjee et al. | | 356/318 |
| 6,128,077 A * | 10/2000 | Jovin et al. | | 356/310 |
| 6,249,348 B1 * | 6/2001 | Jung et al. | | 356/419 |
| 6,496,265 B1 * | 12/2002 | Duncan et al. | | 356/479 |
| 6,598,429 B1 * | 7/2003 | Jiang et al. | | 65/412 |
| 6,831,747 B2 * | 12/2004 | Ferrell et al. | | 356/445 |
| 6,838,660 B2 * | 1/2005 | Duncan et al. | | 250/227.14 |
| 6,975,891 B2 * | 12/2005 | Pawluczyk | | 600/310 |
| 7,268,938 B2 * | 9/2007 | Kawano et al. | | 359/368 |
| 7,385,173 B2 * | 6/2008 | Seyfried et al. | | 250/216 |
| 8,525,988 B2 * | 9/2013 | Schoenfelder et al. | | 356/326 |
| 2001/0007496 A1 * | 7/2001 | Modlin et al. | | 356/73 |

(Continued)

OTHER PUBLICATIONS

Itzkan et al.; Confocal light absorption and scattering spectroscopic microscopy monitors organelles in live cells with no exogenous labels; PNAS; Oct. 30, 2007; vol. 104, No. 44, 17255-17260.

*Primary Examiner* — Kara E Geisel
*Assistant Examiner* — Jarreas C Underwood
(74) *Attorney, Agent, or Firm* — William Greener; Bond, Schoeneck & King, PLLC

(57) ABSTRACT

Apparatus and method to measure optical absorption spectra with spatial resolution on the micron scale. An exemplary setup combines a continuous white light excitation beam in transmission geometry with a GRIN-based detection path in place of a typical confocal microscope. The apparatus and method enables the investigation of spatial variations in the optical density of small samples on the micron scale and the study of biological assemblies at the single cell level, leading to applications in optical diagnostics, microfluidics, cytology, and other areas.

9 Claims, 2 Drawing Sheets

(56) References Cited

U.S. PATENT DOCUMENTS

2003/0016359 A1* 1/2003 Jung et al. .................... 356/419
2004/0046121 A1* 3/2004 Golden et al. ........... 250/339.07
2007/0013917 A1* 1/2007 Stubbe et al. ................. 356/511
2008/0137061 A1* 6/2008 Rush ............................ 356/4.04

* cited by examiner

GRADIENT INDEX (GRIN)-BASED ABSORPTION SPECTROSCOPY APPARATUS, METHOD, AND APPLICATIONS

RELATED APPLICATION DATA

The instant application claims priority to U.S. Provisional Application Ser. No. 61/454,785 filed on Mar. 21, 2011, the subject matter of which is incorporated herein by reference in its entirety.

GOVERNMENT SPONSORSHIP

N/A.

TECHNICAL FIELD

Embodiments of the present invention relate generally to optical systems, associated methods, and applications thereof enabling the measurement of, and use of, spatially resolved optical absorbance and variations in optical density of a sample. More particularly, embodiments pertain to such optical systems, associated methods, and applications directed to gradient-index (GRIN)-based absorption spectroscopy apparatus and methods.

BACKGROUND

The ability to investigate structure and dynamics on a micron scale with non-destructive optical probes is key to studies at the single cell level and applications in microfluidics. Confocal microscopy is a technique that provides enhanced resolution due to elimination of out of focus rays by a spatial filter (pinhole) or by multi-photon excitation. For confocal detection, a pinhole is located in the conjugate plane of the focal plane (defined by the collection optics), which enables optical sectioning along the axial direction.

Fluorescence probes employing confocal or other geometries are well established; however they generally require labeling and are limited by photobleaching and quenching. Micro-spectroscopy based on absorption measurements provides a convenient label free way for characterizing an unknown material. Fourier-transform infrared (FTIR) spectroscopic imaging relying on vibrational signatures has numerous applications. Though light scattering has been used recently as a source of contrast in the visible, standard confocal microscopy so far lacks the capability for direct optical absorption profile measurements.

A difficulty for measurements with axial resolution is presented by the 'missing cone' problem (see, e.g., M. B. Cannell, A. McMorland and C. Soeller, "Image enhancement by deconvolution", *Handbook of biological confocal microscopy*, J. B. Pawley Ed. (Springer, New York, N.Y., 2006), $3^{rd}$ ed., Chap. 25, pp. 488-500). The optical transfer function is angularly band limited, so that the longitudinal resolution in the axial direction is degraded. To provide spatial discrimination in the axial direction, a confocal laser absorption microscope has been reported. An excitation laser pulse irradiates the sample so that ground-state molecules transit to the excited state, thus creating a spatial distribution of molecules, similarly to what is used in confocal fluorescence. The absorption to higher energy levels is then probed by a monitoring laser beam introduced coaxially. An excited state absorption profile is obtained by scanning the sample. In general the absorption of the laser beam due to electronic transitions from the ground state is assumed to be negligible, although the attenuation of the propagating light could provide a mechanism for contrast in the axial direction.

More simply, the lack of adequate spatial resolution limited the ability to practically measure absorbance in a single cell. Small samples let too much light through the system.

The inventors have recognized the advantages and benefits of a practical and robust solution directed especially to enabling micron-scale axial and lateral resolution absorption spectroscopy to study cells in their native environment and other biological assemblies. For example, the ability to acquire micron-scale absorption measurements of single live erythrocytes in femtoliter volume solutions in micro-capillaries or microchannels, and to determine variations in composition of inhomogeneous samples (e. g. thin films of a few microns), to detect malaria, to monitor blood bank quality by measuring absorption spectrum changes in aging blood cells, to monitor body fluids for pregnancy and AIDS testing, for intrinsic imaging, and other applications and capabilities would be advantageous, especially in microfluidics and nano-materials characterization. Further advantages and benefits would be obtained with more compact instrumentation.

SUMMARY

The invention enables a novel transmission-geometry, optical absorbance, micro-spectroscopy apparatus and method to obtain ground state absorption spectra with a spatial resolution in the micron range. The embodied invention employs a GRIN-based detection system to probe and spectrally resolve the attenuation of a non-monochromatic beam in the axial direction. The method enables the measurement of absorption spectra of biological assemblies at the single cell level and of small samples with a thickness of few microns. Transmission geometry, GRIN-based and GRIN-based confocal absorption microscopy is nondestructive and is capable of collecting both spatial and physical information based on light absorption by microscopic structures.

An embodiment of the invention is a transmission-geometry, optical absorbance spectroscopy apparatus for micro-absorption spectroscopy, having a GRIN-based detection path in place of an optical microscope (including an optical confocal microscope). The apparatus includes a transmitted light detection path comprising a gradient index (GRIN)-based optical waveguide having an input end to receive transmitted sample excitation light and an output end for optical coupling to an entrance aperture of a spectrometer. The apparatus may further comprise a stand-alone sample illumination apparatus as described in co-pending U.S. application Ser. No. 13/370,969 and a GRIN lens/optical fiber-based detection path. In various exemplary, non-limiting aspect, the apparatus may further include the following features and/or characteristics:

further comprising a spectrometer;
wherein the GRIN-based optical waveguide further comprises a GRIN lens at the input end and an optical fiber having an input end optically coupled to the GRIN lens and an output end that can be optically coupled to the entrance aperture of a spectrometer;
wherein the GRIN lens has a pitch between about 0.3 to 1.2;
wherein the GRIN-based optical waveguide further comprises an optical coupler disposed between the output end of the GRIN lens and the input end of the optical fiber;
wherein the GRIN lens has a pitch between about 0.1 to 0.3.
wherein the optical coupler is a GRIN lens;

wherein the optical coupler is a lensed optical fiber
wherein the optical fiber is a single mode optical fiber;
wherein the optical fiber is a multi mode optical fiber;
further comprising a translation stage coupled to the GRIN-based optical waveguide;
   wherein the translation stage further includes a lateral two-dimensional scanner and a height positioning device.

An embodiment of the invention is a method for performing transmission-based optical absorption spectroscopy of a sample. The method includes the steps of imaging the illumination light that is transmitted by the sample via a GRIN-based optical waveguide; inputting the imaged light into a spectrometer; and obtaining the optical absorption spectrum of the sample. In various exemplary, non-limiting aspect, the apparatus may further include the following features and/or characteristics:
confocally imaging the illumination light that is transmitted by the sample via the GRIN-based optical waveguide;
wherein the step of imaging the illumination light that is transmitted by the sample via a GRIN-based optical waveguide further comprises providing a GRIN lens adjacent the sample to collect the transmitted light, and an optical fiber having an input end optically coupled to an output of the GRIN lens and an output end optically coupled to the spectrometer;
   further comprising scanning the GRIN lens over a stationary sample;
   further comprising providing an optical coupler between the GRIN lens and the optical fiber;
      further comprising providing a second GRIN lens as the optical coupler;
      further comprising providing a single mode optical fiber;

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

BRIEF DESCRIPTION OF THE DRAWINGS

The present invention will be more fully understood and appreciated by reading the following Detailed Description in conjunction with the accompanying drawings, in which.

DETAILED DESCRIPTION OF NON-LIMITING, EXEMPLARY EMBODIMENTS OF THE INVENTION

Figure 1:
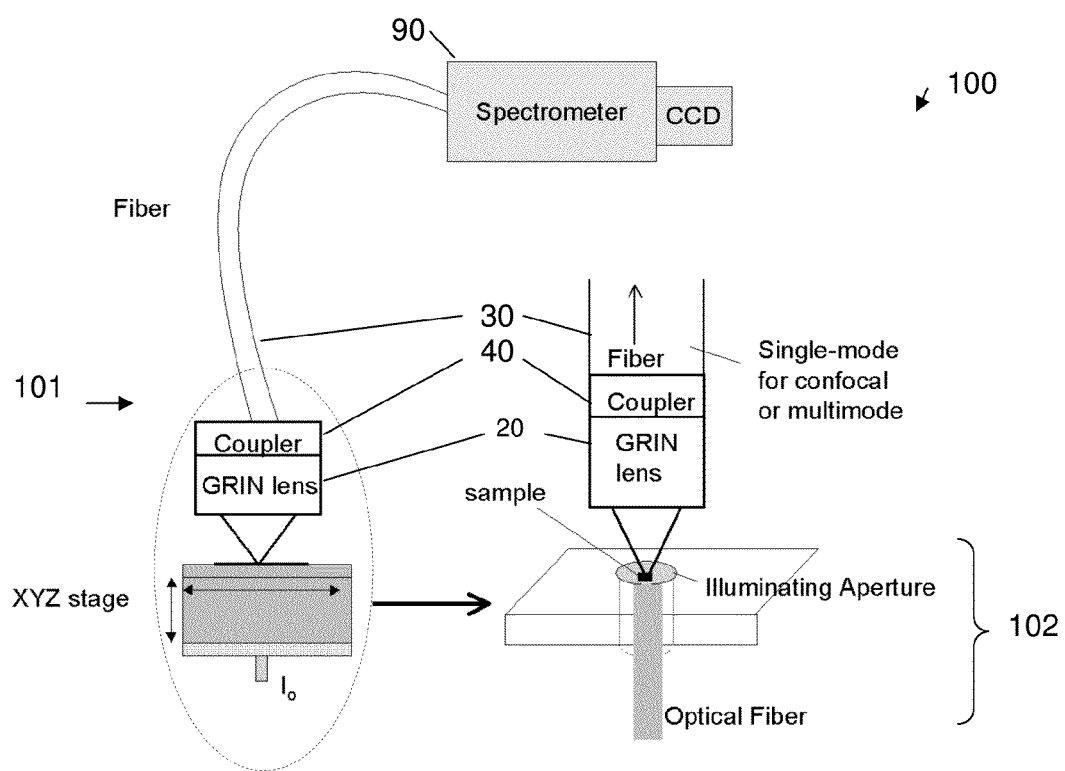
FIG. 1 shows a schematic of a confocal absorption microscopy apparatus according to an exemplary embodiment of the invention.

A transmission-geometry, optical absorbance, spectroscopy apparatus 100 for micro-absorption spectroscopy, having a GRIN-based detection component 101 is shown in FIG. 1. The apparatus 100 includes a sample illumination component 102 that is utilized to illuminate a sample (e.g., a red blood cell) disposed in a micro-capillary or microfluidic channel 102 of a microfluidic device as known in the art. An exemplary sample illumination component is described in co-pending U.S. application Ser. No. 13/370,969, and is not a component of the instant invention per se.

The GRIN-based detection component 101 captures the illumination light that is transmitted (i.e., not absorbed or reflected) through the sample and delivers it to a spectrometer 90. The spectrometer typically has a small (pinhole) entrance aperture that contributes to the confocal detection of the transmitted light. The embodied GRIN-based component significantly simplifies the detection portion of the apparatus as it replaces the microscope objective (and any other free-space confocal imaging components) as illustrated, for example, in U.S. application Ser. No. 13/370,969.

As further shown in FIG. 1, a GRIN lens 20 is positioned adjacent the thin sample to collect the illumination light transmitted there through. The GRIN lens 20 is coupled to an optical fiber 30 via a coupler 40, which may be another GRIN lens. The output end of the fiber 30 can then be coupled to the entrance aperture of the spectrometer 90. An exemplary GRIN lens 20 may have a diameter in the range of less than 0.5 to greater than 1 mm and a pitch between about 0.3 to 1.2 mm when the GRIN lens 20 is directly coupled with the fiber 30; and a pitch between about 0.1 to 0.3 mm when the GRIN lens 20 is coupled with the fiber via an optical coupler 40 as shown. Use of a single mode fiber provides spatial filtering analogous to a pinhole for confocal imaging. Alternatively, a multimode fiber may be used at the expense of decreased resolution in the axial direction.

Referring again to FIG. 1, a method for confocal absorption microscopy involves illuminating the sample as disclosed in U.S. application Ser. No. 13/370,969 and detecting the transmitted light with the above described GRIN-based detection system. As described in the '969 application, a conventional tungsten-halogen lamp was used to illuminate the sample through an optical fiber. A fiber alignment cylinder topped with a field of view-limiting aperture was seated at the center of a sample holder having a V-groove along the longitudinal center for aligning a micro-capillary. The aperture limits the stray light and only allows illumination of the sample inside the micro-capillary. The sample holder was mounted on a 3-D (x-y-z) positioning stage, which allowed scanning the sample through the optical path.

Figure 2:
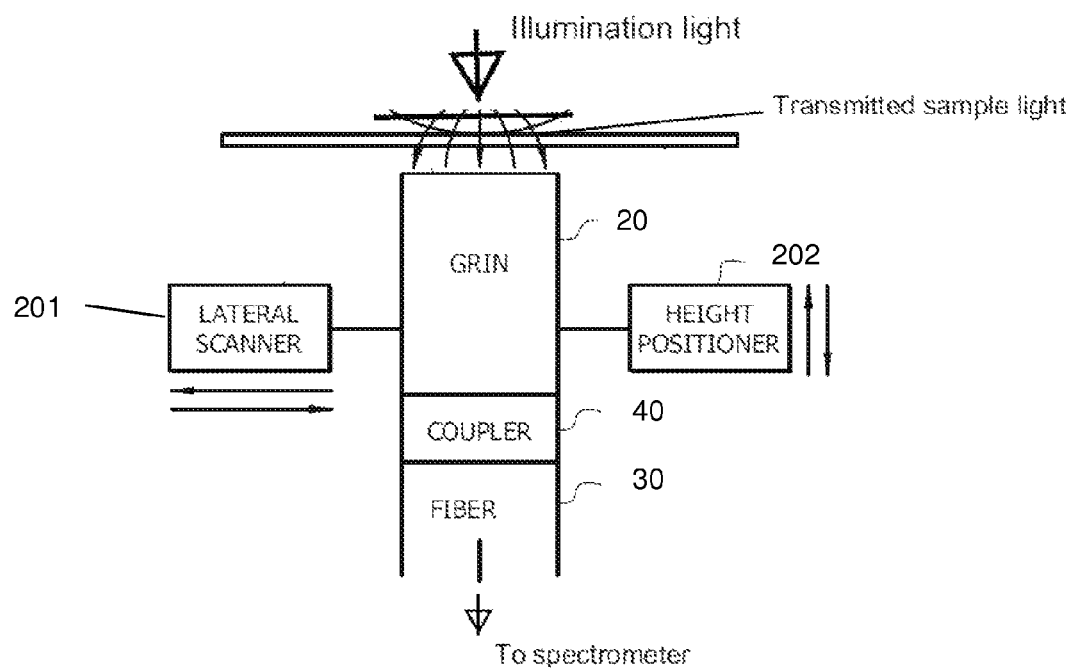
FIG. 2 schematically shows the GRIN-based detection system coupled to a 3-D translation system, according to an exemplary aspect of the invention.

According to an embodied aspect, the GRIN lens (or GRIN assembly) could be fixed and pre-aligned relative to the illumination aperture, and the sample could be attached to a 3-D translation stage. In an alternative aspect, as illustrated in FIG. 2, the sample could be mounted on a stationary assembly in fixed relation to the illuminating aperture, and the GRIN lens 20 (or GRIN assembly 20, 30, 40) could be attached to a 3-D translation stage that allows movement of the GRIN with respect to the sample. The 3-D translation stage could include a lateral (i.e., x-y) scanner 201, which provides the ability to scan GRIN 20 across the surface of the sample, and a height positioning device 201 for controlling the z-axis separation. Spatial resolution is achieved by scanning the GRIN (or GRIN assembly) relative to the sample.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

We claim:

1. A transmission-geometry, optical absorbance spectroscopy apparatus, comprising:
   a confocal spectrometer; and
   a transmitted light detection path comprising a gradient index (GRIN)-based optical waveguide having an input end to receive transmitted sample excitation light and an output end optically coupled to an entrance aperture of the spectrometer,
   wherein the GRIN-based optical waveguide further comprises a GRIN lens at the input end and an optical fiber having an input end optically coupled to the GRIN lens and an output end optically coupled to the entrance aperture of the spectrometer, wherein the GRIN-based optical waveguide further comprises an optical coupler disposed between the output end of the GRIN lens and the input end of the optical fiber, and wherein the optical coupler is a GRIN lens.

2. The apparatus of claim 1, wherein the GRIN lens has a pitch between 0.3 to 1.2.

3. The apparatus of claim 1, wherein the optical fiber is a single mode optical fiber.

4. The apparatus of claim 1, further comprising a translation stage coupled to the GRIN-based optical waveguide.

5. The apparatus of claim 4, wherein the translation stage further includes a lateral two-dimensional scanner and a height positioning device.

6. A method for performing transmission-based, optical micro-absorption spectroscopy of a sample, comprising:
   imaging the illumination light that is transmitted by the sample via a GRIN-based optical waveguide;
   inputting the imaged light into a spectrometer; and
   obtaining the optical absorption spectrum of the sample,
   wherein the step of imaging the illumination light that is transmitted by the sample via a GRIN-based optical waveguide further comprises providing a GRIN lens adjacent the sample to collect the transmitted light, and an optical fiber having an input end optically coupled to an output of the GRIN lens and an output end optically coupled to the spectrometer, further comprising providing an optical coupler between the GRIN lens and the optical fiber, further comprising providing a second GRIN lens as the optical coupler.

7. The method of claim 6, further comprising confocally imaging the illumination light that is transmitted by the sample via the GRIN-based optical waveguide.

8. The method of claim 6, further comprising scanning the GRIN lens over a stationary sample.

9. The method of claim 6, further comprising providing a single mode optical fiber.

* * * * *